United States Patent [19]

Shishkova et al.

[11] 4,178,214

[45] Dec. 11, 1979

[54] CULTURE MEDIUM FOR CULTIVATION OF FODDER YEASTS

[76] Inventors: Zinaida P. Shishkova, ulitsa Struktoru, 4a, kv. 21; Arvid Y. Kalninsh, ulitsa Sverdlova, 8, kv. 3; Juris P. Gailitis, ulitsa Bikernieku, 37, kv. 26; Uldis Y. Shmit, ulitsa Lenina, 118, kv. 21; Nikolai A. Vedernikov, ulitsa Aptiekas, 8, kv. 66; Valter P. Krastinsh, ulitsa Sabiles, 11, kv. 12, all of Riga; Damir A. Kalinkin, ulitsa Volodarskogo, 130, kv. 109, Bobruisk; Viktor R. Vaax, ulitsa Minskaya, 113, kv. 70, Bobruisk; Maria A. Zinina, ulitsa Minskaya, 101, kv. 61, Bobruisk; Vasily D. Belyaev, Sivtsev Vrazhek pereulok, 33, kv. 5, Moscow; Nikolai S. Maximenko, ulitsa Verkhnepervomaiskaya, 59/35, korpus 2, kv. 81, Moscow; Yakov V. Epshtein, 11 Parkovaya ulitsa, 19/21, kv. 126, Moscow, all of U.S.S.R.

[21] Appl. No.: 831,602

[22] Filed: Sep. 8, 1977

[51] Int. Cl.$^2$ .......................... A23K 1/00; A23J 1/18; C12K 1/00; C12C 11/08
[52] U.S. Cl. .................... 435/252; 426/53; 426/60; 426/635
[58] Field of Search ................ 195/100; 426/49, 52, 426/53, 54, 60, 635, 636

[56] References Cited

U.S. PATENT DOCUMENTS

| 1,515,016 | 11/1924 | Earp-Thomas | 195/100 |
| 2,928,740 | 3/1960 | Rosenthal et al. | 426/60 |

OTHER PUBLICATIONS

Soviet Journal "Gidroliznaja Lesokhimicheskaja Promyshlennost", No. 3, 1973, p. 1.

*Primary Examiner*—David M. Naff
*Attorney, Agent, or Firm*—Steinberg & Blake

[57] ABSTRACT

Increased yield of fodder yeasts is obtained with a culture medium containing peat hydrolysate, ligneous waste hydrolysate and sources of nitrogen, phosphorus and potassium. The peat hydrolysate is obtained by hydrolysis of peat with sulphuric acid and the hydrolysate has a pH of 4.0 to 4.4.

5 Claims, No Drawings

CULTURE MEDIUM FOR CULTIVATION OF FODDER YEASTS

The present invention relates to the microbiological industry, and more particularly to culture medium for cultivation of fodder yeasts.

Fodder yeasts are of great importance for the diet of animals and birds as a vitamin-protein additive to low-protein basic fodder. In addition, yeasts contain micro- and macroelements required for the metabolism processes. Yeasts are very valuble insofar as they provide indispensable amino acids.

There is known a culture medium for cultivation of fodder yeasts, including a carbon source, namely, hydrolysate of vegetable matter with pH 4.0–4.4 and containing 1.25–1.75% by weight of dry substance, 1–1.5% by weight of reducing substances (RS), a nitrogen source, a phosphorus source and a potassium source with the following proportions of the components, in % by weight:

hydrolysate of vegetable matter: 98
ammonia water or ammonium sulphate, in terms of nitrogen: 0.02–0.03
ammonium biphosphate or superphosphate, in terms of $P_2O_5$: 0.03–0.45
potassium chloride or sulphate, in terms of potassium: 0.016–0.024
water: the balance (cf. Soviet Journal "Gidroliznaja Lesokhimicheskaja Promyshlennost", No. 3, 1973, p. 1).

The term "hydrolysate of vegetable matter" as used herein, denotes a product of hydrolysis of ligneous wastes (sunflower seed husks, maize stumps, straw), which is obtained in the hydrolysis of plants by treating the above-mentioned materials with diluted sulphuric acid at 120°–130° C. under pressure. The hydrolysate is neutralized to pH=4–4.2 and used as the basic component of a culture medium for cultivation of fodder yeasts.

The yield of the biomass of fodder yeasts with the culture medium of the above composition usually is not higher than 45% by weight of the content of reducing substances (RS). This is due to low biological quality of hydrolysates of vegetable matter as herein defined and insufficient content of physiologically active substances therein.

Also known in the art is a culture medium for cultivation of fodder yeasts, containing hydrolysate of vegetable matter, hydrolysate of keratin wastes which function as a growth stimulator, and sources of nitrogen, phosphorus and potassium. However, this culture medium gives only a slight increase in the yield of the biomass of yeast, by as low as 5–8% by weight. In addition, hydrolysate of keratin wastes contained in the culture medium is hardly available, since the range of stock materials for obtaining keratin is very limited. Collection and transportation of keratin products to hydrolysis plants is a very difficult job.

It is an object of the invention to improve the yield of the biomass of fodder yeasts when cultivating the latter.

The above object is accomplished by the provision of a culture medium for cultivation of fodder yeasts, containing hydrolysate of vegetable matter with pH=4.0–4.4, sources of nitrogen, phosphorus and potassium, which, according to the invention also contains peat hydrolysate with pH=4.0–4.4 with the following proportions of the components, in % by weight:

hydrolysate of vegetable matter: 48–97
peat hydrolysate: 0.1–50
source of nitrogen, in terms of nitrogen: 0.02–0.08
source of phosphorus, in terms of $P_2O_5$: 0.03–0.12
source of potassium, in terms of potassium: 0.016–0.064
water: the balance.

The source of nitrogen may comprise an aqueous solution of ammonia or ammonium sulphate.

The source of phosphorus may comprise ammonium phosphate or calcium superphosphate.

The source of potassium may comprise potassium sulphate or chloride.

The culture medium having the above composition provides an improvement in the yield of the biomass of yeasts up to 70% by weight, in terms of the reducing substances contained therein.

Hydrolysate of vegetable matter in the composition of the culture medium is obtained by using conventional methods, that is, by hydrolysis of wastes of vegetable products with diluted sulphuric acid. The hydrolysate is neutralized to pH=4.0–4.4 and used as the basic component. The hydrolysate of vegetable matter may contain up to 5% by weight of dry substances and up to 4% by weight of reducing substances.

The term "peat hydrolysate" is used herein to denote a product of hydrolysis of peat, obtained by treating peat with a small amount of concentrated sulphuric acid (about 18% in terms of dry weight of peat). The hydrolysis is conducted until oligosaccharides are obtained. Then the hydrolysate is diluted with water to the acid content of about 5% and heated at 110°–120° C. under pressure. Under these conditions, oligosaccharides are converted into monosugars. Hydrolysate of peat containing monosugars is neutralized to pH=4.0–4.4, separated from the precipitate and used as a stimulator in the culture medium for accumulating the biomass of yeasts during cultivation thereof.

For obtaining peat hydrolysate, younger peat should be used, that is upper, slightly decomposed layers of peat. Such peat contains much polysaccharides which are converted, during hydrolysis, into monosugars functioning as a carbon source of microorganisms. Therefore, the addition of peat hydrolysate to the culture medium improves its nutritive value and strongly influences the process of cultivation of microorganisms, in ultimately resulting in an improved yield of the biomass.

As stated above, the amount of peat hydrolysate should be within the range of from 0.1 to 50%. The addition of more than 50% of peat hydrolysate does not result in improved yield of the biomass of yeasts, so that it is inexpedient to add more than 50% of the hydrolysate.

Peat hydrolysate may also be used in the form of a concentrate. For that purpose, peat hydrolysate is concentrated by evaporation to the content of dry substances up to 30–60% by weight. This concentrated peat hydrolysate may be added to the culture medium in an amount of 0.1–5% by weight, and this will suffice to attain the desired result, that is, to improve the yield of the biomass. The use of peat hydrolysate in concentrated form largely facilitates storage and transportation. Therefore, it is preferable to employ the composition of a culture medium for cultivation of yeasts, in which past hydrolysate is used in the form of concentrates, with the proportion of the components being as follows, in % by weight:

hydrolysate of vegetable matter: 90–97
peat hydrolysate: 0.1–5
source of nitrogen, in terms of nitrogen: 0.02–0.08
source of phosphorus, in terms of $P_2O_5$: 0.03–0.12
source of potassium, in terms of potassium: 0.016–0.065
water: the balance.

Addition of peat hydrolysate to the culture medium improves the nutritive value of the culture medium, thus favourably affecting the growth and development of microorganisms. This can be explained by the fact that microorganisms can better and more actively assimilate sources of carbon which they scarcely assimilated hereafter, due to the presence of substances contained in the peat hydrolysate.

Yeasts are cultivated in accordance with conventional techniques adopted in the microbiological industry, that is, continuously and under aeration.

The invention will be better understood from the description of the following examples. Contents are given in % by weight.

EXAMPLE 1

1.2 g of $MH_4H_2PO$ and 0.8 g of KCl were added to 1 l of hydrolysate of ligneous wastes containing 2.7% of RS obtained under industrial conditions, neutralized with ammonia water and milk of lime to pH=4.2 and filtered off from the resultant precipitate.

Introduced into the resultant solution was 0.08 l of peat hydrolysate containing 3% of RS neutralized with ammonia water and milk of lime to pH=4.2 and separated by filtering off from non-hydrolysed residue and gypsum.

Cultivation of fodder yeasts Candida tropicalis in the resultant culture medium was conducted continuously at 35°–37° C. and with pH=4.2–4.4, the pH being adjusted within the above-mentioned limits by using ammonia water. The resultant biomass was separated from the liquor by filtering and dried. The yield of the yeasts was 59.7%, in terms of the total amount of RS.

EXAMPLE 2

5 g of concentrate of peat hydrolysate obtained by evaporation concentration containing 40.8% of dry substance, 1.2 g of $NH_4H_2PO_4$ and 0.8 g of KCl were added to 1 l of hydrolysate of ligneous wastes as in Example 1.

Fodder yeasts Candida tropicalis were cultivated in the resultant culture medium continuously at 35°–37° C. with pH=4.2–4.4, the pH being adjusted within the above-mentioned limits with ammonia water. The resultant biomass was separated from the liquor by filtering and dried. The yield of the yeasts was 60%, in terms of the total amount of RS.

Peat hydrolysate was obtained by mechanical and chemical treatment of younger peat with a moisture content of up to 25% using an auger hydrolyzer in the presence of 92% sulphuric acid used in an amount of 18% by weight of dry peat. The resultant peat hydrolysate was allowed to stay at 120° C. for 20 minutes and neutralized with ammonia water to pH=4.2. This peat hydrolysate was used as a stimulator of the culture medium.

Chemical compositions of peat hydrolysate and hydrolysate of vegetable matter are given in Table 1.

Table 1

| Substances | Content of substances in hydrolysate of vegetable matter with pH = 4.2, % by weight | Content of substances in peat hydrolysate with pH = 4.2, % by weight |
|---|---|---|
| Reducing substances (RS) | 2.580 | 3.790 |
| Humic substances | 0.620 | 1.600 |
| Uronic acids | 0.040 | 0.400 |
| Volatile acids | 0.023 | 0.060 |
| Non-volatile organic acids | — | 0.210 |
| Nitrogen-containing substances, in terms of nitrogen | 0.025 | 0.076 |
| Mineral nitrogen | 0.019 | 0.020 |
| Phosphorus-containing substances, in terms of $P_2O_5$ | 0.025 | 0.048 |
| Iron | traces | 0.152 |

As can be seen from Table 1, the content of humic substances in peat hydrolysate is greater than in hydrolysate of vegetable matter. Peat hydrolysate also contains more nitrogen-containing substances (physiologically active substances) than hydrolysate of vegetable matter. Thus, peat hydrolysate improves the nutritive value of the culture medium used for cultivation of microorganisms, thereby ultimately improving the yield of the biomass.

The influence of peat hydrolysate on the yield of the biomass of fodder yeasts is shown in Table 2.

Table 2

| Content of peat hydrolysate in culture medium, % by weight | Content of RS in culture medium, % by weight | Yield of biomass, in terms of RS % by weight | Content of total protein in biomass of yeasts, % by weight |
|---|---|---|---|
| 0.0 | 2.58 | 45.5 | 48.2 |
| 2.0 | 2.84 | 57.6 | 53.13 |
| 9.0 | 2.57 | 59.2 | 49.0 |
| 20.0 | 2.97 | 60.0 | 49.0 |
| 50.0 | 2.97 | 70.0 | 50.0 |

As can be seen from Table 2, culture medium containing peat hydrolysate improves the yield of the biomass of fodder yeasts in terms of reducing substances (RS) by as much as 27 to 31%, depending on the amount of peat hydrolysate. The content of protein in the biomass of yeasts was increased by 2 to 10% as compared with the yeasts obtained in a culture medium without peat hydrolysate.

What is claimed is:

1. A liquid culture medium for cultivation of fodder yeasts which provide a source of proteins, vitamins and minerals in the diet of animals and birds, said liquid culture medium containing the following components in % by weight:

hydrolysate of ligneous wastes other than peat with pH=4.0–4.4: 48–97 peat hydrolysate obtained by hydrolysis of peat with sulphuric acid and having a pH=4.0–4.4: 0.1–50 nitrogen from a source other than said hydrolysates: 0.02–0.08 phosphorus measured as $P_2O_5$ from a source other than said hydrolysates: 0.03–0.12 potassium from a source other than said hydrolysates: 0.016–0.064 water: the balance.

2. A liquid culture medium as claimed in claim 1, containing said peat hydrolysate in the form of a concentrate containing 30 to 60% by weight of dry substance, with the following proportions of components, in % by weight:
hydrolysate of ligneous wastes other than peat with pH=4.0–4.4: 90–97
peat hydrolysate obtained by hydrolysis of peat with sulfuric acid and having a pH=4.0–4.4: 0.1–5
nitrogen from a source other than said hydrolysates: 0.02–0.08
phosphorous measured as $P_2O_5$ from a source other than said hydrolysates: 0.03–0.12
potassium from a source other than said hydrolysates: 0.016–0.064
water: in balance.

3. Liquid culture medium according to claim 1 wherein said source of nitrogen is an aqueous solution of ammonia or ammonium sulphate.

4. Liquid culture medium according to claim 3 wherein said source of phosphorus is ammonium phosphate or calcium superphosphate.

5. Liquid culture medium according to claim 4 wherein said source of potassium is potassium sulphate of chloride.